United States Patent [19]

Möhring et al.

[11] Patent Number: 4,608,446

[45] Date of Patent: Aug. 26, 1986

[54] PROCESS FOR THE PREPARATION OF LOW MOLECULAR WEIGHT POLYHYDROXYL COMPOUNDS

[75] Inventors: Edgar Möhring, Bergisch-Gladbach; Kuno Wagner; Hanns P. Müller, both of Leverkusen, all of Fed. Rep. of Germany

[73] Assignee: Bayer Aktiengesellschaft, Leverkusen, Fed. Rep. of Germany

[21] Appl. No.: 382,049

[22] Filed: May 25, 1982

Related U.S. Application Data

[63] Continuation of Ser. No. 965,645, Dec. 1, 1978, abandoned.

[30] Foreign Application Priority Data

Dec. 16, 1977 [DE] Fed. Rep. of Germany ....... 2756270

[51] Int. Cl.$^4$ ................. C07C 29/132; C07C 29/136; C07C 31/18
[52] U.S. Cl. ................................. 568/863; 260/410.6; 521/155; 560/263; 568/672
[58] Field of Search ..................................... 568/863

[56] References Cited

U.S. PATENT DOCUMENTS

3,478,112 11/1969 Adam et al. ........................ 568/885
4,301,310 11/1981 Wagner ............................. 568/885

FOREIGN PATENT DOCUMENTS

514342 11/1939 United Kingdom ................ 568/863

Primary Examiner—J. E. Evans
Attorney, Agent, or Firm—Gene Harsh; Joseph C. Gil; Lyndanne M. Whalen

[57] ABSTRACT

The instant invention relates to an improved process for the preparation of low molecular weight polyalcohols by the catalytic hydrogenation of a mixture of different low molecular weight hydroxy aldehydes, hydroxy ketones and optionally also polyhydric alcohols such as is formed from the autocondensation of formaldehyde (such a mixture will hereinafter be referred to as "formose"). The invention also relates to the use of these polyalcohols for the production of polyurethane resins.

9 Claims, No Drawings

PROCESS FOR THE PREPARATION OF LOW MOLECULAR WEIGHT POLYHYDROXYL COMPOUNDS

This application is a continuation of application Ser. No. 965,645, filed Dec. 1, 1978, now abandoned.

BACKGROUND OF THE INVENTION

It has been known since the work by Butlerow and Loew (Ann. 120, 295 (1861) and J. prakt. Chem. 33, 321 (1886) in the previous century that the autocondensation of formaldehyde hydrate (formose synthesis) in the presence of basic compounds such as calcium or lead hydroxide is accompanied by the formation of hydroxy aldehydes and hydroxy ketones. Work on formose synthesis has repeatedly been carried out since then.

In this connection one may refer, for example, to Pfeil, Chem. Berichte 84, 229 (1951); Pfeil and Schroth, Chemische Berichte 85, 303 (1952); R. D. Partridge and A. H. Weiss. Carbohydrate Research 24, 29–44 (1972); the formoses obtained from glyceraldehyde and dihydroxy acetone according to Emil Fischer; German Pat. Nos. 822,385; 830,951 and 884,791, U.S. Pat. Nos. 2,121,981; 2,224,910; 2,692,935 and 2,272,378 and British Pat. No. 513,708. These known processes have certain disadvantages such as poor volume/time yields and, colored by-products. New processes have recently been developed by which virtually colorless formoses free from undesirable by-products can be prepared in high yields with the aid of conventional catalysts.

One of these new processes consists of carrying out the condensation of formaldehyde hydrate in the presence of catalysts consisting of soluble or insoluble lead (II) salts or of lead (II) ions attached to high molecular weight carriers and in the presence of a cocatalyst which consists of a mixture of hydroxy aldehydes and hydroxy ketones which may be obtained from the condensation of formaldehyde hydrate and is characterized by the following molar ratios:

compounds with 3 C atoms/compounds with 4 C atoms: 0.5 to 2.0;
compounds with 4 C atoms/compounds with 5 C atoms: 0.2 to 2.0;
compounds with 5 C atoms/compounds with 6 C atoms: 0.5 to 5.0;

and in which the proportion of components containing from 3 to 6 carbon atoms is at least 75% by weight, preferably more than 85% by weight, based on the total quantity of cocatalyst.

The reaction temperature is generally between 70° and 110° C., preferably between 80° and 100° C., and the pH of the reaction solution is adjusted by controlled addition of an inorganic or organic base, first to 6.0 to 8.0, preferably 6.5 to 7.0 up to a conversion of 10 to 60%, preferably 30 to 50%, and thereafter to 4.0 to 6.0, preferably 5.0 to 6.0. It is surprisingly found that the proportions of products in the mixture of polyols, hydroxy aldehydes and hydroxy ketones can be varied in a reproducible manner by this special control of the pH followed by cooling at different residual formaldehyde contents (0 to 10% by weight, preferably 0.5 to 6% by weight).

When the autocondensation of formaldehyde hydrate has been stopped by cooling and/or by inactivation of the lead catalyst with acids, the catalyst, and optionally also the water contained in the products, is removed. Further details of this procedure may be found in German Offenlegungsschriften Nos. 2,639,084 and 2,732,077.

According to German Offenlegungsschrift No. 2,714,084, highly concentrated colorless formoses may also be produced with high volume/time yields by condensing aqueous formalin solutions and/or paraformaldehyde dispersions in the presence of a soluble or insoluble metal catalyst and in the presence of a co-catalyst which has been prepared by partial oxidation of a dihydric or higher hydric alcohol which contains at least two adjacent hydroxyl groups and has a molecular weight of from 62 to 242 or a mixture of such alcohols. The pH of the reaction solution is controlled by controlled addition of a base so that it is maintained at 6.0 to 9.0 until conversion is 5 to 40% complete and is then adjusted to a value from 4.5 to 8.0 until the condensation reaction is stopped so that in this phase of the reaction it is lower by 1.0 to 2.0 units than in the first reaction phase. The reaction is then stopped by inactivation of the catalyst when the residual formaldehyde content is from 0 to 10% by weight, and the catalyst is removed.

High quality formoses can also be prepared by the condensation of formaldehyde in the presence of a metal catalyst and more than 10% by weight, based on formaldehyde, of one or more dihydric or higher hydric low molecular weight alcohols and/or relatively high molecular weight polyhydroxyl compounds (see German Offenlegungsschrift No. 2,714,104).

According to another process, it is particularly economical to prepare formose directly from formaldehyde-containing synthesis gases, i.e. without first preparing aqueous formalin solutions or paraformaldehyde.

For this purpose, the synthesis gases such as can be obtained from the large scale industrial production of formaldehyde are conducted continuously or intermittently at temperatures of from 10° to 150° C. into an absorption liquid which consists of water, monohydric or polyhydric low molecular weight alcohols and/or relatively high molecular weight polyhydroxyl compounds and/or compounds capable of enediol formation as co-catalyst and/or soluble or insoluble metal compounds as catalyst, optionally bound to a high molecular weight carrier, which absorption liquid is at a pH of from 3 to 10. The formaldehyde is directly condensed in situ in the absorption liquid (optionally also in a reaction tube or cascade of stirrer vessels following the container for the absorption liquid), and autocondensation of the formaldehyde is stopped by cooling and/or by inactivation of the catalyst with acids when the residual formaldehyde content in the reaction mixture is from 0 to 10% by weight. The catalyst is finally removed.

For some purposes, mixtures of hydroxy aldehydes, hydroxy ketones and optionally polyalcohols of the kind obtained by the processes described above or by processes known in the art are required to be converted into mixtures of polyalcohols by reduction of the carbonyl group. Such polyol mixtures obtained by the reduction of formoses will hereinafter be referred to as "formite". It is possible, for example, to reduce formose with sodium borohydride from aqueous solution at room temperature (see R. D. Partridge, A. H. Weiss and D. Todd, Carbohydrate Research 24 (1972), 42; but reduction of formose may also be carried out electrochemically, for example.

Many processes are already known for the catalytic hydrogenation of sugars and of formose. Widely differing quantities and types of catalysts are employed, depending on the process. Thus L. Orthner and E. Gerisch Biochem. Zeitung 259, 30 (1933), for example, describe a process for the catalytic hydrogenation of formose in which a 4% aqueous solution of formose is hydrogenated with 170% by weight, based on the quantity of formose, of Raney nickel by a reaction carried out for 7 to 8 hours at 130° C. under a hydrogen pressure of 120 bar. Such a process is, of course, economically unsatisfactory in every respect. In U.S. Pat. No. 2,269,935, a process has been disclosed in which a solution containing approximately 40% by weight of formose is hydrogenated at an acid pH with 20% by weight of nickel catalyst at a hydrogen pressure of 600 to 620 bar and at 120° C. The disadvantage of this variation of the process lies not only in the high operating pressure but also in the low pH, which results in products which are colored green by nickel ions.

In U.S. Pat. No. 2,224,910 a process has been disclosed for the hydrogenation of formose, in which a 40% formose solution is hydrogenated with 30% by weight of Raney nickel, based on the quantity of formose, at a hydrogen pressure of 140 to 210 bar and pH 7 for 4 hours. This process is also unsatisfactory because of the large amount of catalyst required and the long reaction time.

Other hydrogenation processes have been described in German Pat. Nos. 705,274; 725,842; 830,951; 888,096 and 1,004,157 and in U.S. Pat. Nos. 2,271,083; 2,272,378; 2,276,192; 2,760,983 and 2,775,621. All of these processes, however, have one or more of the following disadvantages: considerable outlay in apparatus and difficulty of handling owing to the high hydrogen pressures; large consumption of catalyst, based on the quantity of hydrogenated product (10 to 200% by weight); discolored products due to long hydrogenation times (1 to 10 hours).

Common to all of the known processes is the use of metal catalysts and in some cases noble metal catalysts. Raney nickel, which is commonly used, develops its full activity only in the alkaline range. However, since formoses have a strong tendency to caramelize and give rise to severely discolored products in an alkaline medium, the processes known in the art are generally carried out at a slightly acid or neutral pH.

It was therefore an object of the present invention to provide a process for the rapid hydrogenation of formose with little capital expenditure and very small quantities of catalyst.

DESCRIPTION OF THE INVENTION

It has now surprisingly been found that, contrary to the view hitherto held in the literature, formoses which may be mixed with other natural or synthetic sugars, can be rapidly hydrogenated to colorless polyol mixtures in an alkaline medium with only small quantities of catalyst, at hydrogen pressures of from 100 to 200 bar and temperatures of from 50° to 250° C. This is new and in view of the above-mentioned caramelization reactions of formose, which take place particularly rapidly in an alkaline medium at elevated temperatures, it is also completely unexpected. One would indeed have expected dark colored to black products to be produced.

It must also be regarded as surprising that in the polyalcohol mixtures obtained by the process according to the invention, the proportion of low molecular weight $C_2$-, $C_3$- and $C_4$-alcohols is substantially higher than in formites produced by conventional processes. This is particularly advantageous for various applications.

The present invention thus relates to a process for the preparation of low molecular weight, polyhydric alcohols by the reduction of formose at a temperature of from 80° to 220° C. under a hydrogen pressure of from 50 to 300 bar in the presence of a metal catalyst, in which process (1) a solution of formose at a concentration of at least 20%, preferably more than 35% and most preferably more than 45% is introduced batchwise into a reactor maintained at a temperature of from 100° to 200° C., most preferably at 140° to 190° C., in such an amount that the proportion of reducible groups, determined as carbonyl groups, in the product mixture contained in the reactor does not exceed 2% by weight and preferably does not exceed 1% by weight and most preferably not 0.5% by weight;

(2) the pH is adjusted to a value in the range of from 7.5 to 12.5, preferably from 8.5 to 11.5, immediately before the hydrogenation reaction;

(3) the total quantity of catalyst used is from $10^{-4}$ to $5 \times 10^{-2}$% by weight, based on the total quantity of starting material which is to be reduced, the catalyst content remaining constant in the reactor;

(4) the reaction product is withdrawn batchwise from the reactor when the proportion of reducible groups, determined as carbonyl groups, has fallen below 0.15% by weight, and preferably below 0.05% by weight.

The process according to the invention is advantageously carried out as follows:

The quantity of catalyst, preferably Raney nickel, required for the hydrogenation of the entire batch is introduced into water in a pressure reactor. The reactor is filled with gaseous hydrogen to the operating pressure of 50 to 300 bar and then heated to the hydrogenation temperature of from 80° to 220° C. From three to thirty times the quantity, preferably five to twenty times, of formose solution, based on the catalyst, is then slowly pumped in (i.e. about 1/6th of the capacity of the reactor) within 3 minutes to 2 hours, preferably 5 to 30 minutes. Hydrogenation is then continued for a period ranging from half to four times the time which was required for pumping in the solution. The quantity of reaction mixture corresponding to the quantity of formose solution pumped in is then forced out through a steel-jacketed frit while the catalyst is left in the reactor. A new batch is then pumped into the reactor and treated in the same way as the first batch. All subsequent batches are treated in the same manner.

This batchwise hydrogenation by pumping according to the invention results in an extremely long catalyst life and hence, based on the total quantity of formose which is reduced or to be reduced, very low catalyst consumption.

In this connection, it should be pointed out again that the long catalyst life which can be achieved according to the invention is completely surprising since, in view of the caramelization reactions of formose which would be expected to take place in an alkaline medium, it would be expected that the catalyst would be inactivated by the products.

The process according to the invention for production of hydrogenated sugars or hydrogenated formose ("formite") affords the following important advantages over the known art:

1. The process according to the invention is highly economical. Compared with all known processes, it requires an extremely small amount of catalyst. The hydrogenation velocity is very high; for example, only 10 to 15 minutes are required for each hydrogenation step at high temperatures (150° to 190° C.).

2. The process according to the invention can be carried out without great capital outlay since, in view of the relatively low pressures employed, no special apparatus or safety measures are necessary.

3. The process according to the invention results in light colored or colorless products which can be used for a wide variety of purposes without further purification.

4. One surprising and special advantage of the process is the substantial splitting of the starting materials into low molecular $C_2$-to $C_5$-alcohols, whereby the viscosity of the polyhydroxyl compounds is lowered, their processibility is improved and at the same time their compatibility with other substances is increased, especially with the starting components used for the production of synthetic resins by the polyisocyanate polyaddition process (in particular higher molecular weight polyhydroxyl compounds and blowing agents).

5. Another special advantage is that, if desired, other compounds, e.g. alkanals, alcohols (e.g. $C_1$ to $C_{23}$, in particular $C_1$ to $C_8$ alcohols, which may be either mono- hydric or polyhydric), ketones, aldehydes or higher molecular weight polyols may be present during hydrogenation, particularly because they improve the compatibility of the reaction products with the blowing agents used for the polyisocyanate polyaddition process. These aldehydes, ketones and alkanals may be added in quantities of up to 50% by weight (based on the total quantity of substances which are to be reduced).

6. Not only formose but other natural and synthetic sugars may also be hydrogenated by the process according to the invention.

The aldehydes or alkanals which may also be used in the process according to the invention include in particular acetaldehyde, propionaldehyde, butyraldehyde, isobutyraldehyde and their methylol derivatives.

The ketones used may be acetone, methylethyl ketone, diethyl ketone, cyclopentanone, cyclohexanone, mesityloxide, isophorone, acetophenone, benzophenone and their methylol derivatives.

The solvent used in the process according to the invention is mainly water although the formoses may be dissolved in any monohydric or polyhydric alcohols. Examples of suitable alcohols include methanol; ethanol; propanol; butanol; isopropanol; isobutanol; cyclopentanol; cyclohexanol; 2-ethoxy-ethanol; 2-propoxyethanol; 2-isopropoxyethanol; 2-butoxy-ethanol; 2-(2-methoxyethoxy)-ethanol; 2-(2-ethoxyethoxy)-ethanol; 1,2-bis-(2-hydroxyethoxy)-ethane; ethylene glycol, diethylene glycol; triethylene glycol; tetraethylene glycol; 1,2-propanediol; isopropylene glycol; 1,3-propanediol; 1,2-butanediol; 1,3-butanediol; 2-methoxy-1-butanol; 2,3-butane-diol; 1,5-pentanediol; 2,2-dimethyl-1,3-propanediol; 1,6-hexanediol; 2,5-hexanediol; 2-methyl-2,4-pentanediol; 3-methyl-1,5-pentanediol; 3-methyl-2,4-pentanediol; 2,3-dimethyl-2,3-butanediol; 2-methyl-2-propyl-1,3-propanediol; 2,2-diethyl-1,3-propanediol; 2-ethyl-1,3-hexanediol; 2,5-dimethyl-2,5-hexanediol; 2,2,4-trimethyl-1,3-pentanediol; 1,3-diethoxy-2-propanol; 2-hydroxymethyl-2-methyl-1,3-propanediol; 1,2,6-hexanetriol; 2-ethyl-2-hydroxymethyl-1,3-propanediol; 2,2-bis-hydroxymethyl-1,3-propanediol; erythritol; quinitol; mannitol; sorbitol; methyl glycoside and ethoxylation and propoxylation products of these alcohols with a molecular weight of up to about 400 and, of course, also mixtures of these alcohols. Ethylene glycol, glycerol and 1,4-butanediol are particularly preferred.

According to the invention, polyhydroxyl compounds having a molecular weight of from 400 to 10,000, preferably from 500 to 6,000, may also be used for the hydrogenation of formose, optionally as mixtures with the above mentioned alcohols. These polyhydroxyl compounds are preferably also liquid at room temperature or soluble in the formose solution. For example, the polyesters, polyethers, polythioethers, polyacetals, polycarbonates and polyester amides containing at least 2, generally from 2 to 8, preferably from 2 to 4 hydroxyl groups, of the type commonly used for the production of homogeneous and cellular polyurethanes may be used.

The hydrogenation process according to the invention is applicable to any formoses obtained by the known processes described above. The formose may also be used as a mixture with up to 80% by weight, based on the total quantity of compounds to be hydrogenated, of other artificial or natural sugars, e.g. glucose, maltose, fructose, saccharose, lactose, etc. One advantage of formose used in such mixtures is that it is an excellent solvent or solubilizing agent for such sugars.

The artificial invert sugars which may also be used according to the invention may be hydrolysates of any di- and/or polysaccharides e.g. hydrolysates of cane sugar, mixtures of cane sugar and invert sugars, hydrolysates of trehalose, maltose or isomaltose, hydrolysates of corn and potato starch and of pectins (amylose and amylopectins), cellobiose and lactose, hydrolysates of galactose, glucose mixtures, raffinose hydrolysates, cellulose hydrolysates, hydrolysates of dextrins optionally mixed with unhydrolyzed dextrins, hydrolysates of Schardinger dextrins (cyclic dextrins) hydrolysates of glycogen, hydrolysates of glucose-6-phosphoric acid, hydrolysates of glucose-1-phosphate (coriesters), fructose-6-phosphate, degraded pectins (polygalacturonic acids), degraded glucosamines and hydrolysates of molasses residues, etc.

The pH of the solution which is to be hydrogenated may be adjusted with either inorganic or organic bases. Sodium hydroxide, potassium hydroxide, calcium hydroxide, magnesium hydroxide, barium hydroxide, aluminum hydroxide, triethylamine, N-methyl morpholine and N-methyl piperidine are preferably used. It is particularly preferred to use the base which has been used for the synthesis of the formose and which has been converted into the free OH form before hydrogenation by treatment of the formose solution with the ion exchange resin in the OH form. In that case, the formose solution automatically adjusts itself to the required alkalinity.

The hydrogenation catalysts used for the process according to the invention are mainly metals with atomic numbers 23 to 29, in the elementary and/or oxidic form. Suitable catalysts include, for example, those based on nickel or cobalt. As carriers for the catalysts there may be used both inorganic materials such as Kieselguhr, silicates, aluminum oxides, alkali metal and alkaline earth metal silicates, aluminum silicates, montmorillonite, zeolithes, spinells, dolomite, kaolin, magnesium silicates, zirconium oxide, iron oxide, zinc oxide, calcium carbonate, silicon carbide, aluminum phosphate, boron phosphate, asbestos or active charcoal and organic materials such as naturally occurring or synthetic high molecular weight compounds such as silk, polyamides, polystyrenes, cellulose or polyurethanes. The carrier may be in the form of pellets, strands, filaments, cylindrical shapes, polygons or powders. It is preferred to use Raney-type catalysts such as Raney-nickel, W-1-, W-5-, W-6- and W-7-Raney nickel (see H. Adkins, J. Am. Chem. Soc. 69, 3039 (1974)), Raney-cobalt catalysts, Raney-copper, Raney-nickel-iron, Raney-cobalt-nickel and Raney-cobalt-iron. Metal catalysts obtained by the reduction of nickel or cobalt salts may also be used; for example, urushibara nickel, nickel or cobalt salts which have been reduced with metal alkyl compounds, alkali metal hydrides, hydrazines, boranates or hydrogen boride, catalysts prepared by the reduction of metal oxides or metal oxide mixtures, or the metal oxides or metal oxide mixtures themselves.

The preferred catalysts according to the invention, which are based on metals with atomic numbers 23 to 29, may contain up to 10% by weight of one or more of the following elements as accelerators:

Li, Na, Ca, Ba, K, Ag, Be, La, Ce, V, Nb, Ta, Mo, W and up to 1% by weight of the elements Ru, Rh, Pd, Au, Ir, and Pt.

Raney nickel containing 90% by weight of Ni and <1% by weight of Fe, Ca and Na, Raney nickel iron containing from 5 to 30% by weight of Fe and <1% by weight of Ca and Na, and Raney cobalt-iron containing from 10–30% by weight of Fe are particularly suitable catalysts.

The mixtures of polyhydric low molecular weight alcohols prepared according to the invention are most preferably used as polyol components for the polyisocyanate polyaddition process.

The present invention thus also relates to a process for the preparation of cellular or non-cellular polyurethane resins by the reaction of (a) a polyisocyanate with (b) a compound with a molecular weight of from 32 to 400 which contains at least two active hydrogen atoms, optionally (c) a compound with a molecular weight of from 400 to 10,000 containing at least two active hydrogen atoms, and optionally (d) blowing agents, catalysts and other known additives, which process is characterized in that component (b) consists entirely or partly of a mixture of low molecular weight polyhydric alcohols prepared according to the invention.

The polyisocyanates used as starting components according to the invention may be aliphatic, cycloaliphatic, araliphatic, aromatic or heterocyclic polyisocyanates such as those described, for example, by W. Siefken in Justus Liebigs Annalen der Chemie, 562, pages 75 to 136. Examples include ethylene diisocyanate; tetramethylene-1,4-diisocyanate; hexamethylene-1,6-diisocyanate; dodecane-1,12-diisocyanate; cyclobutane-1,3-diisocyanate; cyclohexane-1,3- and -1,4-diisocyanate and any mixtures of these isomers; 1-isocyanato-3,3,5-trimethyl-5-isocyanatomethylcyclohexane (German Auslegeschrift No. 1,202,785 and U.S. Pat. No. 3,401,190); hexahydrotolylene-2,4-diisocyanate and -2,6-diisocyanate and any mixtures of these isomers; hexahydrophenylene-1,3-diisocyanate and/or 1,4-diisocyanate; perhydrodiphenylmethane-2,4'-diisocyanate and/or 4,4'-diisocyanate; phenylene-1,3-diisocyanate and -1,4-diisocyanate; tolylene-2,4-diisocyanate and -2,6-diisocyanate and any mixtures of these isomers; diphenylmethane-2,4'-diisocyanate and-/or 4,4'-diisocyanate; naphthylene-1,5-diisocyanate; triphenylmethane-4,4',4''-triisocyanate; polyphenyl-polymethylene polyisocyanates which can be obtained by aniline-formaldehyde condensation followed by phosgenation and which have been described, for example in British Pat. Nos. 874,430 and 848,671; m- and p-isocyanatophenyl-sulphonyl isocyanates as described in U.S. Pat. No. 3,454,606; perchlorinated aryl polyisocyanates such as those described in U.S. Pat. No. 3,277,138; polyisocyanates having carbodiimide groups as described in U.S. Pat. No. 3,152,162; diisocyanates of the kind described in U.S. Pat. No. 3,492,330; polyisocyanates with allophanate groups as described e.g. in British Pat. No. 994,890, Belgian Pat. No. 761,626 and published Dutch patent application No. 7,102,524; polyisocyanates with isocyanurate groups, e.g. as described in U.S. Pat. No. 3,001,973, German Pat. Nos. 1,022,789; 1,222,067 and 1,027,394 and German Offenlegungsschriften Nos. 1,929,034 and 2,004,048; polyisocyanates with urethane groups as described e.g. in Belgian Pat. No. 752,261 or U.S. Pat. No. 3,394,164; polyisocyanates with acylated urea groups as described in German Pat. No. 1,230,778; polyisocyanates with biuret groups as described e.g. in German Pat. No. 1,101,394; U.S. Pat. Nos. 3,124,605 and 3,301,372 and British Pat. No. 889,050; polyisocyanates prepared by telomerization reactions as described for example, in U.S. Pat. No. 3,654,106; polyisocyanates containing ester groups, such as those described, for example, in British Pat. Nos. 965,474, and 1,072,956; U.S. Pat. No. 3,567,763 and German Pat. No. 1,231,688; reaction products of the above mentioned isocyanates with acetals as described in German Pat. No. 1,072,385; and polyisocyanates containing polymeric fatty acid groups as described in U.S. Pat. No. 3,455,883.

The distillation residues obtained from the commercial production of isocyanates and still containing isocyanate groups may also be used, optionally as solutions in one or more of the above mentioned polyisocyanates. Any mixtures of the above mentioned polyisocyanates may also be used.

As a general rule, it is particularly preferred to use readily available polyisocyanates such as tolylene-2,4-diisocyanate and -2,6-diisocyanate and any mixtures of these isomers ("TDI"); polyphenyl-polymethylene polyisocyanates of the kind which can be prepared by aniline-formaldehyde condensation followed by phosgenation ("crude MDI"); and polyisocyanates containing carbodiimide groups, urethane groups, allophanate groups, isocyanurate groups, urea groups, or biuret groups ("modified polyisocyanates").

The starting components used according to the invention may also include compounds with a molecular weight of generally 400 to 10,000, which contain at least two isocyanate-reactive hydrogen atoms. These compounds may contain amino groups, thiol groups or carboxyl groups but are preferably polyhydroxyl compounds, and in particular compounds having from two to eight hydroxyl groups. Especially preferred are polyhydroxyl compounds having molecular weights of from 800 to 10,000, preferably 1,000 to 6,000, e.g. polyesters, polyethers, polythioethers, polyacetals, polycarbonates and polyester amides containing at least two, generally two to eight, but preferably two to four hydroxyl groups, of the kind which are generally known for the production of both homogeneous and cellular polyurethanes.

Suitable polyesters with hydroxyl groups include e.g. reaction products of polyhydric, and preferably dihydric alcohols (to which trihydric alcohols may be added) and polybasic, preferably dibasic, carboxylic acids. Instead of free polycarboxylic acids, the corresponding polycarboxylic acid anhydrides or corresponding polycarboxylic acid esters of lower alcohols or mixtures thereof may, of course, be used for preparing the polyesters. The polycarboxylic acids may be aliphatic, cycloaliphatic, aromatic and/or heterocyclic and they may be substituted, e.g. by halogen atoms, and/or unsaturated.

The following are mentioned as examples: Succinic acid; adipic acid; suberic acid; azelaic acid; sebacic acid; phthalic acid; isophthalic acid; trimellitic acid; phthalic acid anhydride; tetrahydrophthalic acid anhydride; hexahydrophthalic acid anhydride; tetrachlorophthalic acid anhydride; endomethylene tetrahydrophthalic acid anhydride; glutaric acid anhydride; maleic acid, maleic acid anhydride; fumaric acid; dimeric and trimeric fatty acids such as oleic acid which may be mixed with monomeric fatty acids; dimethyl terephthalate and terephthalic acid-bis-glycol esters. The following are examples of suitable polyhydric alcohols: Ethylene glycol; propylene glycol-(1,2) and -(1,3); butylene glycol-(1,4) and -(2,3); hexanediol-(1,6); octanediol-(1,8); neopentylglycol; cyclohexanediol methanol (1,4-bis-hydroxymethylcyclohexane); 2-methyl-1,3-propanediol; glycerol; trimethylolpropane; hexanetriol-(1,2,6); butanetriol-(1,2,4); trimethylolethane; pentaerythritol; quinitol; mannitol and sorbitol; methyl glycoside; diethylene glycol; triethylene glycol; tetraethylene glycol; polyethylene glycols; dipropylene glycol; polypropylene glycols; dibutylene glycol and polybutylene glycols. The polyesters may also contain a proportion of carboxyl end groups. Polyesters of lactones such as ε-caprolactone or hydroxycarboxylic acids such as ω-hydroxycaproic acid may also be used.

The polyethers used according to the invention which have at least two, generally two to eight and preferably two to three hydroxyl groups are also known per se and are prepared, for example, by polymerization of epoxides such as ethylene oxide, propylene oxide, butylene oxide, tetrahydrofuran, styrene oxide or epichlorohydrin, either each on its own, e.g. in the presence of boron trifluoride, or by addition of these epoxides, either as mixtures or successively, to starting components which have reactive hydrogen atoms, such as water, alcohols, ammonia or amines. Suitable alcohols and amines include ethylene glycol, propylene glycol-(1,3) or -(1,2), trimethylolpropane, 4,4'-dihydroxydiphenylpropane, aniline, ethanolamine or ethylene diamine. Sucrose polyethers may also be used according to the invention, e.g. those described in German Auslegeschriften Nos. 1,176,358 and 1,064,938. It is in many cases preferred to use polyethers which contain predominantly primary hydroxyl groups (up to 90% by weight, based on all the hydroxyl groups present in the polyether). Polyethers modified with vinyl polymers, e.g. the compounds obtained by polymerization of styrene or acrylonitrile in the presence of polyethers (U.S. Pat. Nos. 3,383,351; 3,304,273; 3,523,093 and 3,110,695 and German Pat. No. 1,152,536) are also suitable, as are polybutadienes which contain hydroxyl groups.

Particularly to be mentioned among the polythioethers are the condensation products obtained by reacting thiodiglycol on its own and/or with other glycols, dicarboxylic acids, formaldehyde, aminocarboxylic acids or amino alcohols. The products obtained are polythio mixed ethers, polythio ether esters or polythio ether ester amides, depending on the cocomponents.

Suitable polyacetals include, for example, the compounds which can be prepared from glycols such as diethylene glycol, triethylene glycol, 4,4'-dioxethoxydiphenyl dimethylmethane, hexanediol and formaldehyde. Suitable polyacetals for the purpose of the invention may also be prepared by the polymerization of cyclic acetals.

The polycarbonates with hydroxyl groups used may be of the kind already known, for example those which can be prepared by the reaction of diols such as propanediol-(1,3), butanediol-(1,4) and/or hexanediol-(1,6), diethylene glycol, triethylene glycol or tetraethylene glycol with diarylcarbonates, e.g. with diphenylcarbonate or phosgene.

Suitable polyester amides and polyamides include, for example, the predominantly linear condensates prepared from polyvalent saturated and unsaturated carboxylic acids or their anhydrides and polyvalent saturated and unsaturated amino alcohols, diamines, polyamines and mixtures thereof.

Polyhydroxyl compounds already containing urethane or urea groups and modified or unmodified natural polyols such as castor oil, carbohydrates or starch may also be used. Addition products of alkylene oxides and phenol formaldehyde resins or of alkylene oxides and urea formaldehyde resins are also suitable for the purpose of the invention.

Representatives of these compounds which may be used according to the invention are known and have been described, for example, in High Polymers, Vol. XVI, "Polyurethanes, Chemistry and Technology" by Saunders-Frisch, Interscience Publishers, New York, London, Volume I, 1962, pages 32–42 and pages 44–54 and Volume II, 1964, pages 5–6 and 198–199 and in Kunststoff-Handbuch, Volume VII, Vieweg-Hochtlen, Carl-Hanser-Verlag, Munich, 1966, pages 45 to 71.

Mixtures of the above mentioned compounds which contain at least two isocyanate-reactive hydrogen atoms and have a molecular weight of from 400 to 10,000 may, of course, also be used, for example mixtures of polyethers and polyesters.

The starting components used according to the invention may also include compounds with a molecular weight of from 32 to 400 which have at least two isocyanate-reactive hydrogen atoms. These compounds are also understood to be compounds containing hydroxyl groups and/or amino groups and/or thiol groups and/or carboxyl groups, preferably hydroxyl groups and/or amino groups, and they serve as chain lengthening agents or cross-linking agents. They generally have from two to eight isocyanate-reactive hydrogen atoms, preferably two or three such hydrogen atoms.

The following are examples of such compounds: Ethylene glycol, propylene glycol-(1,2) and -(1,3), butylene glycol-(1,4) and -(2,3), pentanediol-(1,5), hexanediol-(1,6), octanediol-(1,8), neopentyl glycol, 1,4-bis-hydroxymethylcyclohexane, 2-methyl-1,3-propanediol, glycerol, trimethylol propane, hexanetriol-(1,2,6), trimethylolethane, pentaerythritol, quinitol, mannitol and sorbitol, diethylene glycol, triethylene glycol, tetraethylene glycol, polyethylene glycols with a molecular weight of up to 400, dipropylene glycol, polypropylene glycols with a molecular weight of up to 400, dibutylene glycol, polybutylene glycols with a molecular weight of up to 400, 4,4'-dihydroxy-diphenyl propane, dihydroxymethyl-hydroquinone, ethanolamine, diethanolamine, triethanolamine, 3-aminopropanol, ethylene diamine, 1,3-diaminopropane, 1-mercapto-3-aminopropane, 4-hydroxyphthalic acid, 4-aminophthalic acid, succinic acid, adipic acid, hydrazine, N,N-dimethylhydrazine, 4,4'-diaminodiphenylmethane, tolylenediamine, methylene-bis-chloroaniline, methylene-bis-anthranilic acid ester, diaminobenzoic acid esters and the isomeric chlorophenylene diamines.

In this case again, mixtures of various compounds having a molecular weight of from 32 to 400 and containing at least two isocyanate-reactive hydrogen atoms may be used.

Polyhydroxyl compounds which contain high molecular weight polyadducts or polycondensates in a finely dispersed or dissolved form may also be used according to the invention. Such modified polyhydroxyl compounds are obtained when polyaddition reactions, e.g. reactions between polyisocyanates and amino functional compounds or polycondensation reactions, e.g. between formaldehyde and phenols and/or amines are carried out in situ in the above mentioned hydroxyl compounds. Processes of this kind have been described, for example, in German Auslegeschriften Nos. 1,168,075 and 1,260,142 and in German Offenlegungsschriften Nos. 2,324,134; 2,423,984; 2,512,385; 2,513,815; 2,550,796; 2,550,797; 2,550,833 and 2,550,862. These modified polyhydroxyl compounds may also be obtained according to U.S. Pat. No. 3,869,413 or German Offenlegungsschrift No. 2,500,860 by mixing a previously prepared aqueous polymer dispersion with a polyhydroxyl compound and then removing the water from the mixture. When modified polyhydroxyl compounds of this type are used as starting components in the polyisocyanate polyaddition process, the polyurethane resins obtained in many cases have substantially improved mechanical properties.

According to the invention, water and/or readily volatile organic substances may be used as blowing agents. Suitable organic blowing agents include, for example, acetone, ethyl acetate and halogen substituted alkanes such as methylene chloride, chloroform, ethylidene chloride, vinylidene chloride, monofluorotrichloromethane, chlorodifluoromethane, and dichlorodifluoromethane as well as butane, hexane, heptane and diethyl ether. The effect of a blowing agent can also be obtained by the addition of compounds which decompose at temperatures above room temperature to release gases such as nitrogen, e.g. azo compounds such as azoisobutyric acid nitrile. Further examples of blowing agents and the use of blowing agents have been described in Kunststoff-Handbuch, Volume VII, published by Vieweg and Höchtlen, Carl-Hanser-Verlag, Munich 1966, e.g. on pages 108 and 109, 453 to 455 and 507 to 510.

Catalysts are also frequently used according to the invention. The catalysts added may be known per se, for example tertiary amines such as triethylamine; tributylamine; N-methylmorpholine; N-ethylmorpholine; N-cocomorpholine; N,N,N',N'-tetramethylethylenediamine; 1,4-diazabicyclo-(2,2,2)-octane; N-methyl-N'-dimethylaminoethyl-piperazine; N,N-dimethylbenzylamine; bis-(N,N-diethylaminoethyl)-adipate; N,N-diethylbenzylamine; pentamethyldiethylenetriamine; N,N-dimethylcyclohexylamine; N,N,N',N'-tetramethyl-1,3-butanediamine; N,N-dimethyl-$\beta$-phenylethylamine; 1,2-dimethylimidazole and 2-methylimidazole. Mannich bases known per se which have been obtained from secondary amines such as dimethylamine and aldehydes, preferably formaldehyde, or ketones such as acetone, methyl ethyl ketone or cyclohexanone and phenols such as phenol, nonylphenol or bis-phenol may also be used as catalysts.

Examples of tertiary amines with isocyanate-reactive hydrogen atoms which may be used as catalysts include triethanolamine; triisopropanolamine; N-methyl-diethanolamine; N-ethyl-diethanolamine and N,N-dimethyl-ethanolamine and their reaction products with alkylene oxides such as propylene oxide and/or ethylene oxide. Silaamines with carbon-silicon bonds as described e.g. in German Pat. No. 1,229,290, corresponding to U.S. Pat. No. 3,620,984, may also be used as catalysts, e.g. 2,2,4-trimethyl-2-silamorpholine or 1,3-diethylamino-methyl-tetramethyl-disiloxane.

Basic nitrogen compounds such as tetraalkylammonium hydroxides, alkali metal hydroxides such as sodium hydroxide, alkali metal phenolates such as sodium phenolate and alkali metal alcoholates such as sodium methylate may also be used as catalysts. Hexahydrotriazines are also suitable catalysts.

Organic metal compounds may also be used as catalysts according to the invention, in particular organic tin compounds.

The organic tin compounds used are preferably tin (II) salts of carboxylic acids such as tin (II) acetate, tin (II) octoate, tin (II) ethyl hexoate and tin (II) laurate and tin (IV) compounds such as dibutyl tin oxide, dibutyl tin dichloride, dibutyl tin diacetate, dibutyl tin dilaurate, dibutyl tin maleate or dioctyl tin diacetate. All of the above mentioned catalysts may, of course, be used as mixtures.

Further examples of catalysts which may be used according to the invention and details concerning the activity of the catalysts are described in Kunststoff-Handbuch, Volume VII, published by Vieweg and Hochtlen, Carl-Hanser-Verlag, Munich 1966, pages 96 to 102.

The catalysts are generally used in a quantity of between about 0.001 and 10% by weight, based on the quantity of formite.

Surface active additives such as emulsifiers and foam stabilizers may also be used according to the invention. Suitable emulsifiers include e.g. the sodium salts of ricinoleic sulphonate or salts of fatty acids with amines such as oleic acid diethylamine or stearic acid diethanolamine. Alkali metal or ammonium salts of sulphonic acids such as dodecylbenzenesulphonic acid or dinaphthylmethane disulphonic acid or of fatty acids such as ricinoleic acid or of polymeric fatty acids may also be used as surface active additives.

Suitable foam stabilizers are particularly the polyether siloxanes, and especially those which are water-soluble. These compounds generally have a polydimethyl siloxane group attached to a copolymer of ethylene oxide and propylene oxide. Foam stabilizers of this kind have been described, for example, in U.S. Pat. Nos. 2,834,748; 2,917,480 and 3,629,308.

Other additives which may also be used according to the invention include reaction retarders, e.g. substances which are acid in reaction such as hydrochloric acid or organic acid halides; cell regulators known per se such as paraffins, fatty alcohols or dimethyl polysiloxanes; pigments; dyes; flame retarding agents known per se such as tris-chloroethylphosphate, tricresyl phosphate or ammonium phosphate or polyphosphate; stabilizers against ageing and weathering; plasticizers; fungistatic and bacteriostatic substances; and fillers such as barium sulphate, kieselguhr, carbon black or whiting.

Other examples of surface active additives, foam stabilizers, cell regulators, reaction retarders, stabilizers, flame retarding substances, plasticizers, dyes, fillers and fungistatic and bacteriostatic substances which may be used according to the invention and details concerning the use and mode of action of these additives may be found in Kunststoff-Handbuch, Volume VII, published by Vieweg and Höchtlen, Carl-Hanser-Verlag, Munich 1966, pages 103 to 113.

According to the invention, the components are reacted together by the known one-shot, prepolymer or semiprepolymer process, often using mechanical devices such as those described in U.S. Pat. No. 2,764,565. Details concerning processing apparatus which may also be used according to the invention may be found in Kunststoff-Handbuch, Volume VII, published by Vieweg and Höchtlen, Carl-Hanser-Verlag, Munich, 1966, pages 121 to 205.

According to the invention, the reaction for producing foams is often carried out inside molds. In this process, the foamable reaction mixture is introduced into a mold which may be made of a metal such as aluminum or a plastics materials such as an epoxide resin, and it foams up inside the mold to produce the shaped product. This process of foaming in molds may be carried out to produce a product having a cellular structure on its surface or it may be carried out to produce a product having a compact skin and cellular core. According to the invention, one or other result can be obtained as desired by either introducing just sufficient foamable reaction mixture to fill the mold with foam after the reaction or introducing a larger quantity of reaction mixture than is necessary to fill the mold with foam. The second method is known as "overcharging", a procedure which has already been disclosed, e.g. in U.S. Pat. Nos. 3,178,490 and 3,182,104.

So-called "external mold release agents" known per se, such as silicone oils, are frequently used when foaming is carried out inside molds but the process may also be carried out with the aid of so-called "internal mold release agents", if desired as mixtures with external mold release agents, e.g. as disclosed in German Offenlegungsschriften Nos. 2,121,670 and 2,307,589.

Cold setting foams may also be produced according to the invention by the processes described in British Pat. No. 1,162,517 and German Offenlegungsschrift No. 2,153,086.

Foams may, of course, also be produced by the process of block foaming or by the laminator process known per se.

The method of reacting only the polyhydroxyl compounds which are obtainable according to the invention, without the addition of other isocyanate reactive components, with strongly elasticizing polyisocyanates such as polyisocyanates which have a biuret structure as described in German Auslegeschrift No. 1,543,178, results in hard, light-fast, scratch resistant and solvent resistant coatings and lacquers.

Polyether alcohols with a high functionality can be obtained by basic or acid catalyzed propoxylation and/or ethoxylation of the polyols. Among these polyether alcohols, those which have high hydroxy numbers may be used for the manufacture of rigid or semi-rigid cellular polyurethane resins whereas those with low hydroxyl numbers are suitable starting materials for highly elastic polyurethane foams. Further details concerning the preparation of polyethers may be found in German Offenlegungsschrift No. 2,639,083.

Highly branched polyesters which may be used as additives to alkyd resins to improve their hardness can be obtained by reacting the mixtures of polyhydric alcohols prepared according to the invention with polybasic carboxylic acids of the type mentioned above, such as phthalic acid, isophthalic acid, terephthalic acid, tetra- and hexahydrophthalic acid, adipic acid or maleic acid by the usual methods of polyester condensation, for example as described in Houben Weyl, Methoden der organischen Chemie, Volume XIV 12, page 40. The hydroxyl-containing polyesters synthesized from the hydroxyl compounds which have been prepared according to the invention are, of course, also suitable as starting components for the production of polyurethane resins.

The polyhydric alcohols prepared according to the invention may also easily be reacted with long chain, aliphatic monocarboxylic acids such as caprylic, capric, lauric, myristic, palmitic, stearic, oleic, linoleic, arachidonic or behenic acid or their derivatives, e.g. their methyl or ethyl esters, or their anhydrides or mixed anhydrides, to produce hydroxyl-containing esters. These esters, like the ethoxylation products of the polyols or the carbamic acid esters obtained by reacting the polyhydroxyl compounds prepared according to the invention with long chain monoisocyanates such as n-octyl, n-decyl, n-dodecyl, myristyl, cetyl or stearyl isocyanate (see e.g. K. Lindner, Tenside Volume III, Wissenschaftliche Verlagsgesellschaft Stuttgart 1964, page 2336), are non-ionogenic, surface active compounds which are valuable emulsifiers, wetting agents and plasticizers. The compounds according to the invention may also be used as moisturizers in cosmetics and synthetic resins.

They may also be used, for example, as anti-freezes or as additives in formulations for plant protection.

The following examples serve to explain the process according to the invention. Quantities given represent parts by weight of percentages by weight unless otherwise indicated.

Examples 3 and 4 show that the quantity of catalyst required is very small.

EXAMPLES

Example 1 (Comparison Example)

This example shows that in processes known in the art, using much longer times and larger quantities of catalyst, a higher proportion of $C_6$–$C_8$ components is obtained than in the process according to the invention.

250 ml of a formose solution according to Example 1 of German Offenlegungsschrift No. 2,721,186 are hydrogenated with 80 g of Raney nickel in a 0.7 liter autoclave at a hydrogen pressure of 150 bar for 4 hours at 30° C., then for 1 hour at 60° C. and finally for 1 hour at 100° C.

A slightly yellowish solution of polyhydroxyl compounds containing 0.018% of reducing groups and having the following molecular distribution is obtained:

Compounds containing 2 C atoms: 0.8
Compounds containing 3 C atoms: 2.2
Compounds containing 4 C atoms: 5.6
Compounds containing 5 C atoms: 30.4

-continued

Compounds containing 6 C atoms: 40.0
Compounds containing 7 or more C atoms: 21.0

Example 2 (Comparison Example)

This example shows that neither adjustment of the pH to an alkaline value nor increase in temperature alone is capable of producing the low molecular weight distribution of components obtained in the following examples.

250 ml of the formose solution from Example 1 are adjusted to pH=10 and hydrogenated with 80 g of Raney nickel in a 0.7 liter autoclave at 150 bar hydrogen pressure for 30 minutes. The temperature is raised from 30° C. to 100° C. during this time. The solution is hydrogenated for 1 hour at 100° C. and then for 1 more hour at 140° C. A colorless solution in which no more reducing constituents can be detected and which has the following molecular distribution is obtained:

Compounds containing 2 C atoms: 3.2
Compounds containing 3 C atoms: 8.0
Compounds containing 4 C atoms: 12.6
Compounds containing 5 C atoms: 33.6
Compounds containing 6 C atoms: 27.0
Compounds containing 7 or more C atoms: 16.6

General Method of Hydrogenation (Examples 3 and 4)

100 parts of catalyst (C) in 300 parts of water are introduced into a 3 liter refined steel autoclave and heated to the hydrogenation temperature (T). The volume above the water is then filled with hydrogen gas at the operating pressure (P). 500 parts of a 50% formose solution prepared according to Example 1 of German Offenlegungsschrift No. 2,721,186, containing 11.1% of reducible groups (determined as carbonyl groups) are adjusted to the required pH and then pumped into the autoclave within a predetermined pumping time (PT). Hydrogenation is then continued for a fixed period of time (HT). 500 parts of solution are then discharged through an upright pipe containing a frit which holds back the catalyst. The process is repeated with the next batch of formose solution containing 500 parts. Hydrogenation is continued until the activity of the catalyst falls or until the required number of cycles has been performed or the required quantity of product has been obtained. No loss of catalyst was found to occur even after many cycles of hydrogenation. The hydrogenated solutions are collected and freed from most of the water in them by evaporation under vacuum. Colorless to pale yellowish formites which can be worked up without further purification are obtained in all cases. If desired, the solutions may be completely desalted over ion exchange resins. The distribution of components indicated was calculated from gas chromatographic analyses.

Example 3

This example shows that in the process according to the invention, hydrogenation may be carried out with very little consumption of catalyst.

| pH = 10.0 | P = 150 bar | T = 100° C. |
| PT = 25 min. | HT = 25 min. | C = Raney nickel/ |
| | | iron (85%/15%) |

| Batch Number | % > C = 0 |
| --- | --- |
| 1 | 0.016 |
| 2 | 0.016 |
| 3 | 0.016 |
| 4 | 0.016 |
| 5 | 0.016 |
| 6 | 0.016 |
| 7 | 0.016 |
| 8 | 0.016 |
| 9 | 0.016 |
| 10 | 0.016 |
| 20 | 0.031 |
| 30 | 0.031 |
| 40 | 0.031 |
| 50 | 0.031 |
| 100 | 0.040 |
| 150 | 0.023 |
| 200 | 0.029 |
| 250 | 0.020 |
| 300 | 0.028 |
| 350 | 0.014 |
| 400 | 0.032 |

A colorless solution having the following molecular distribution is obtained:

| Compounds containing | | |
| --- | --- | --- |
| | 2 C atoms: | 3.9% by weight |
| | 3 C atoms: | 20.7% by weight |
| | 4 C atoms: | 24.1% by weight |
| | 5 C atoms: | 22.4% by weight |
| | 6 C atoms: | 22.0% by weight |
| | 7 or more: | 6.8% by weight |

Example 4

This example shows that hydrogenation can be effected very rapidly with little consumption of catalyst by the process according to the invention.

| pH = 10.5 | P = 150 bar | T = 140° C. |
| PT = 6 min | HT = 6 min | C = Raney nickel/ |
| | | iron (85%/15%) |

| Batch number | % > C = 0 |
| --- | --- |
| 1 | 0.005 |
| 2 | 0.005 |
| 3 | 0.006 |
| 4 | 0.008 |
| 5 | 0.006 |
| 6 | 0.005 |
| 7 | 0.006 |
| 8 | 0.006 |
| 9 | 0.012 |
| 10 | 0.012 |
| 20 | 0.014 |
| 30 | 0.014 |
| 40 | 0.025 |
| 50 | 0.031 |
| 100 | 0.034 |
| 150 | 0.042 |
| 200 | 0.027 |
| 260 | 0.023 |

A colorless solution having the following molecular distribution is obtained:

| Compounds containing | | |
| --- | --- | --- |
| | 2 C atoms: | 6.8% by weight |
| | 3 C atoms: | 19.3% by weight |
| | 4 C atoms: | 22.3% by weight |
| | 5 C atoms: | 19.0% by weight |
| | 6 C atoms: | 20.0% by weight |
| | 7 or more: | 12.6% by weight |

Example 5

Preparation of a polyurethane foam.

25 parts of a polypropylene oxide (hydroxyl number 74) which has been started on ethylenediamine,
22 parts of the formite from Example 3,
10 parts of trichloroethyl phosphate,
15 parts of monofluorotrichloromethane,
0.5 parts of dimethylbenzylamine,
0.5 parts of a commercial silicone stabilizer (L-5420 of UCC) and
75 parts of a commercial phosgenation product of aniline/formaldehyde condensates (isocyanate content: 29%)

are mixed vigorously and the resulting mixture is left to foam up in an open mold. A rigid, fine celled foam which has high tear resistance and dimensional stability is obtained.

What is claimed is:

1. A process for producing low molecular weight, polyhydric alcohols by reducing formose in the presence of a metal catalyst comprising:
   (a) introducing said metal catalyst into a reaction vessel;
   (b) raising the temperature in said reaction vessel to from 80° to 220° C.;
   (c) introducing hydrogen into said reaction vessel at a pressure of from 50 to 300 bars;
   (d) adjusting the pH of a formose solution to between 7.5 and 12.5;
   (e) introducing batch-wise into said reaction vessel said formose solution at a concentration of at least 20%, characterized in that the proportion of reducible groups determined as carbonyl groups, in the mixture inside said reaction vessel does not exceed 2% by weight, further characterized in that said formose solution is introduced in an amount of from 3 to 30 times the amount of catalyst introduced;
   (f) conducting a reduction reaction until the proportion of reducible groups, determined as carbonyl groups, falls below 0.15% by weight;
   (g) removing reaction product from said reaction vessel in an amount equal to the amount of said formose solution introduced in step (e) and allowing said catalyst to remain in said reaction vessel;
   (h) repeating steps (b) through (g) until the desired quantity of reaction product has been obtained.

2. The process of claim 1, characterized in that the individual batches are pumped in at a rate which corresponds to filling 1/6th of the volume of the reactor in from 3 to 120 minutes.

3. The process of claim 2, characterized in that the rate of filling corresponds to 1/6th of the volume of the reactor in from 5 to 30 minutes.

4. The process of claim 3, characterized in that after each batch has been pumped in, hydrogenation is continued for from ½ to 4 times the time required for pumping in the batch.

5. The process of claim 1, characterized in that up to 80% by weight (based on the total quantity of products to be hydrogenated) of other natural or synthetic sugars are added to the formose.

6. The process of claim 1, characterized in that catalysts which contain nickel are used.

7. The process of claim 6, characterized in that the catalyst used is Raney nickel optionally modified with iron.

8. A process as claimed in claim 1, wherein said metal catalyst is used for at least 400 batches.

9. The product of the process of claim 1.

* * * * *